United States Patent [19]

Tozzi

[11] Patent Number: 5,153,182
[45] Date of Patent: Oct. 6, 1992

[54] INSECTICIDE COMPOSITIONS CONTAINING METHYLENE-DIOXYBENZENE DERIVATIVES AS SYNERGISTS

[75] Inventor: Antonio Tozzi, Bologna, Italy

[73] Assignee: Endura S.p.A., Italy

[21] Appl. No.: 652,246

[22] Filed: Feb. 6, 1991

Related U.S. Application Data

[63] Continuation of Ser. No. 405,216, Sep. 11, 1989, abandoned, which is a continuation-in-part of Ser. No. 150,250, Jan. 29, 1988, abandoned.

[30] Foreign Application Priority Data

Feb. 16, 1987 [IT] Italy ................................ 19389 A/87

[51] Int. Cl.$^5$ ..................... A01N 43/30; A01N 53/00; A01N 43/04; A01N 35/00
[52] U.S. Cl. ...................... 514/67; 514/102; 514/450; 514/464; 549/445
[58] Field of Search ............... 514/67, 102, 450, 464; 549/445

[56] References Cited

U.S. PATENT DOCUMENTS

| | | | |
|---|---|---|---|
| 2,485,681 | 10/1949 | Wachs | 549/445 |
| 2,550,737 | 1/1951 | Wachs | 514/464 |
| 3,070,607 | 12/1962 | Barthel et al. | 549/445 |
| 3,117,135 | 1/1964 | Hedenburg | 549/445 |

FOREIGN PATENT DOCUMENTS

| | | | |
|---|---|---|---|
| 61-24586 | 2/1986 | Japan | 549/445 |
| 1159089 | 7/1969 | United Kingdom | 549/445 |

OTHER PUBLICATIONS

Sumitomo, C.A., 99, 171334 (1983).
Cornforth et al., 72, 66609y (1970).
Moore et al., J. Sci. Food Agric., pp. 666–672 (1958).
The Pesticide Manual, (1983 ed.) pp. 150, 427, 438, 479, 520.
J. Casida et al., vol. 153, Science, pp. 1130–1133 (1966).

*Primary Examiner*—Nicky Chan
*Attorney, Agent, or Firm*—Parkhurst, Wendel & Rossi

[57] ABSTRACT

Insecticided compositions comprising (a) a mixture of methylenedioxybenzene derivative compounds having in the benzene ring one, two and three substituents of the formula $-CH_2O-(CH_2CH_2O)_2-R_1$ wherein $R_1$ is hydrogen or an alkyl group having from 1 to 4 carbon atoms and (b) an insecticide selected from the group consisting of synthetic pyrethroids, carbamates, organic phosphorates, avermentines and insect growth regulators.

4 Claims, No Drawings

INSECTICIDE COMPOSITIONS CONTAINING METHYLENE-DIOXYBENZENE DERIVATIVES AS SYNERGISTS

CROSS-REFERENCE TO RELATED APPLICATION

This is a continuation of application Ser. No. 07/405,216 filed Sep. 11, 1989, now abandoned, which is a continuation-in-part of U.S. patent application Ser. No. 150,250, filed on Jan. 29, 1988, now abandoned.

FIELD OF THE INVENTION

This invention relates to insecticidal compositions containing methylenedioxybenzene derivatives possessing synergistic action on various classes of insecticides and to a method for combating insects with the composition of the invention.

BACKGROUND OF THE INVENTION

Methylenedioxybenzene derivatives of the general formula

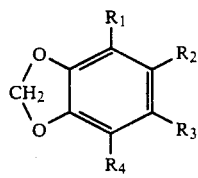

in which $R_1$, $R_2$, $R_3$ and $R_4$, are hydrogen or alkyl group or a halogen atom or a group

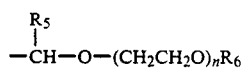

wherein $R_5$ represents hydrogen or an alkyl group and $R_6$ represents an alkyl group, are currently used as synergists for certain insecticides.

Wachs in U.S. Pat. No. 2,485,681 and U.S. Pat. No. 2,550,737 describes methylenedioxybenzene derivatives of the formula

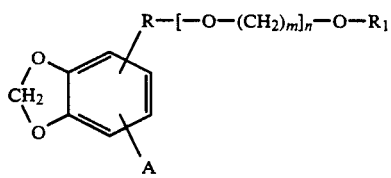

in which A is hydrogen or an aliphatic radical, R is an intermediate aliphatic radical, $R_1$ is a hydrocarbon radical, m is 2 or more and n is 1 or more, in admixture with natural pyrethrins. One of the compounds under the scope of the Wachs patents is piperonyl butoxide, in which R is $CH_2$, m is 2, n is 2, $R_1$ is butyl and A is propyl. Such compound is widely used as a synergist for natural pyrethrins.

Barthel et al, in U.S. Pat. No. 3,070,607, describe compounds of the formula

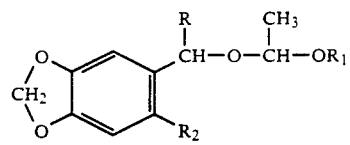

in which R is hydrogen, methyl, or ethyl; $R_1$ is alkoxyalkyl or polyalkoxyalkyl; $R_2$ is hydrogen, propyl, propenyl or allyl, to be used as synergists for natural and synthetic pyrethrins. Hedenburg, in U.S. Pat. No. 3,117,135, describes compounds of the formula

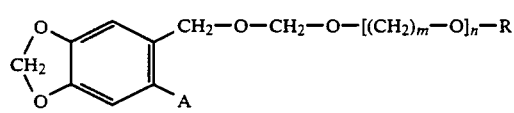

wherein R is alkyl of from 1 to 4 carbon atoms, m is 2 or 3 and n is 1 or 2 and A is propyl or allyl, to be used as synergists for natural and synthetic pyrethrins.

British patent 1,159,089 describes compounds of the formula

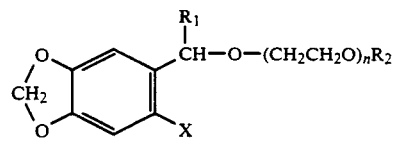

wherein $R_1$ is hydrogen or an alkyl group, $R_2$ is alkyl group and X is a halogen atom or the same

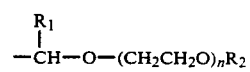

group as above, to be used as synergist for pyrethrins.

Japanese patent application 58-110,504 (as reported in C.A. 99,171334) of Sumitomo describes compounds of the formula

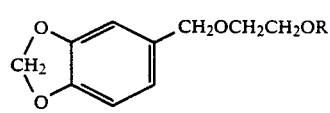

wherein R is $CH_3$ or $CH_2CH_2OC_4H_9$ to be used in controlling pyrethroid-resistant insects.

Japanese patent application 61-24586 of Sumitomo describes compounds of the formula

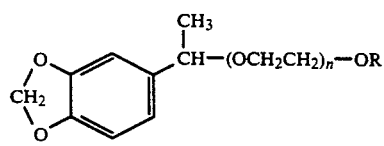

wherein R is hydrogen or lower alkyl and n is 1, 2 or 3, to be used as synergists for pyrethroids, fenvalerate and carbamate type insecticides.

B. P. Moore and P. S. Hewlett, in J. Sci. Food Agric. Oct. 9, 1958, 666, describes the relatioshionship between chemical structure and synergistic activity with natural pyrethrins in methylenedioxybenzene compounds of graded complexity. There are described compounds of the formula

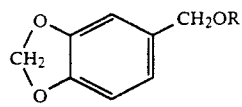

wherein R is $(CH_2)_2-O-(CH_2)_6-CH_3$ or $(CH_2CH_2O)_3-CH_3$. According to the publication, the synergism is specific to the methylenedioxy benzene group.

J. E. Casida et al., in Science 153, 1131 (1966), describing the metabolism of various methylenedioxybenzene compounds in relation to their synergistic action, state that such compounds synergize the insecticidal activity of almost all classes of insecticide chemicals. Piperonyl butoxide is reported.

Of all the above mentioned compounds, the most currently used as synergist for insecticides is piperonyl butoxide, which however is quite expensive, being prepared only from safrole, which in turn is obtained only from essential oils, notably of sassofrass. Safrol is listed as a carcinogen by the EPA.

Anyway, in all of the above patents and publications, there are used, as synergists, pure methylenedioxybenzene derivative compounds, which means that such compounds, whatever was their preparation, were isolated from the reaction mixture.

SUMMARY OF THE INVENTION

The present invention is directed to the unexpected discovery that a mixture of three methylenedioxybenzene derivatives, having the formulas:

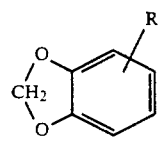 (II)

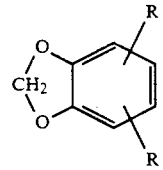 (III)

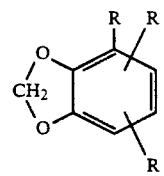 (IV)

wherein R is $CH_2O(CH_2CH_2O)_2R_1$ and $R_1$ is hydrogen or an alkyl group with from 1 to 4 carbon atoms, has the same or even a superior synergistic effect than that of the same weight amount of the well known compound piperonylbutoxide, if used in combination with insecticides selected from the group consisting of synthetic pyretroids, carbamates, organic phosphorates, avermectines and insect growth regulators.

The result is surprising, because the prior art teaches that the methylenedioxybenzene group is responsible for the synergistic action of the methylenedioxybenzene derivatives. In piperonylbutoxide the weight content of methylenedioxybenzene is 35% and is remarkably lower in the mixture of the invention.

If $R_1$ in formulas (II), (III) and (IV) is $C_4H_9$, in a mixture according to the invention having compounds of formulas (II), (III) and (IV) in a molar ratio 0.3:0.6:0.1 the methylene dioxybenzene weight content is 28%. Therefore, for this reason one would expect that the mixture of the invention would possess a much lower synergistic activity than the one of pyperonylbutoxide. Thus, the discovery that such mixtures possess an equivalent or even superior activity is unexpected and surprising.

DETAILED DESCRIPTION OF THE INVENTION

The present invention concerns insecticidal compositions comprising (a) a mixture of methylenedioxybenzene derivative compounds of formulas (II), (III) and (IV) above and (b) an insecticide selected from the group consisting of synthetic pyrethroids, carbamates, organic phosphorates, avermectines and insect growth regulators.

In the mixture of methylene dioxybenzene derivatives, the compounds of formula (II) are present in a molar amount of from 10 to 50%; the compounds of formula (III) in a molar amount of from 30 to 70% and the compounds of formula (IV) in a molar amount of from 5 to 20%.

In the insecticidal composition the weight ratio of components (a) and (b) is between 100:1 and 1:1.

The mixtures of compounds of formulas (II), (III) and (IV) are prepared by reaction of methylenedioxybenzene with hydrochloric acid and formaldeyde. According to the proportions between the reactants and operating conditions, different mixtures of the following compounds are obtained:

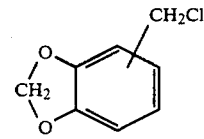 (V)

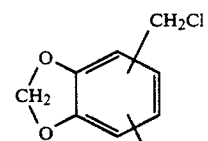 (VI)

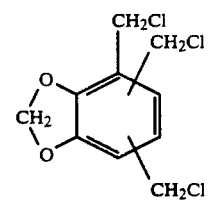 (VII)

By reacting the mixtures of compounds (V), (VI) and (VII) with an excess of alcohols of the general formula $HO(CH_2CH_2O)_2R_1$, wherein $R_1$ has the aforesaid meaning, in the presence of proton acceptors, at a temperature of between 20° and 100° C., in a medium consisting of an organic solvent such as benzene, mixtures of compounds (II), (III) and (IV) are obtained.

Another way of obtaining the mixtures of compounds (II), (III) and (IV) is to react mixtures of compounds (V), (VI) and (VII) with sodium alcoholates of formula NaO(CH$_2$CH$_2$O)$_2$R$_1$, used in slight excess over the chlorine content of the chlorinated methylenedioxybenzene derivatives.

The mixtures of the present invention are used as synergists in association with:

(a) synthetic pyrethroids such as: allethrin, permethrin, tetramethrin, resmethrin, cyfenthrin, fenfluthrin, fenproparthrin and also compounds which are generally considered as pyrethroids even if they do not have the usual cyclopropane ring, such as fenvalerate and fluvalinate, and their resolved isomers;

(b) carbamate insecticides, such as carbaryl and propoxur;

(c) organic phosphorate insecticides, such as dichlorvos and chlorpyrifos;

(d) avermectines;

(e) insect growth regulators, such as diflubenzuron, methoprene and hydroprene.

The following examples will further illustrate the invention. It will be understood, however, that these examples are not intended to be limitative as to the scope of the invention.

EXAMPLE 1

Preparation of the mixture of the invention. In a glass flask of 500 ml equipped with stirrer and thermometer there are introduced 45.8 grams of methylenedioxybenzene, 29.2 grams of paraformaldehyde and 270 ml of 37% HCl. The temperature is raised to 55° C. and kept at this value for 2 hours and 30 minutes. The reaction is controlled with a gaschromatograph.

First the monosubstituted chloromethylated compound only is obtained; this is then partially transformed into the bisubstituted compound and later on also the trisubstituted compound is formed. The reaction mixture is then put in a separator and the water layer is discarded.

The organic layer is treated with 120 ml of benzene; after agitation the solution is neutralized with solution of sodium bicarbonate, thereafter water is eliminated with sodium sulphate.

The above solution is added gradually to a benzene solution of Na O(CH$_2$CH$_2$O)$_2$C$_4$H$_9$ (which was previously prepared by reacting at the boiling temperature 112 grams of the corresponding alcohol, 37 grams of Na OH and 112 ml of benzene, until water was no longer produced).

When the addition is completed, the whole mass is agitated at the boiling temperature for 2 hours. After cooling, sodium chloride is filtrated, the solution is washed with water and thereafter treated with sodium sulphate. Finally, by distilling under vacuum, benzene and non-reacted alcohol are eliminated. Then are obtained 131 grams of a product, which has the following composition (by gaschromatographic analysis):

| | |
|---|---|
| Monosubstituted product (II) | 29.8% by weight |
| Bisubstituted product (III) | 55.1% by weight |
| Trisubstituted product (IV) | 10.6% by weight |
| Impurities | 4.5% by weight |

The molar ratio between (II), (III) and (IV) is therefore 0.43:0.50:0.07.

By changing the ratio between methylenedioxybenzene and paraformaldeyde and the reaction time, products having different molar ratio between compounds (II), (III) and (IV) are obtained.

EXAMPLE 2

Comparative tests were carried out on *Blatta orientalis*, using the following formulations:

| | | |
|---|---|---|
| insecticide | 0.1–1.0% | by weight |
| synergist | 0.45–1.0% | by weight |
| isopropyl alcohol | 10.0% | by weight |
| aerosol propellent | 50.0% | by weight |
| n-dodecane | 38–39.4% | by weight (as much as suffices to 100) |
| | 100 | |

The synergists used had the following composition:
PBO: piperonylbutoxide
PBX.1: mixture of the invention, in which the molar ratio between compounds of formulas (II) (III) and (IV) was: 0.43:0.50:0.07.
PBX.2: as in PBX.1, in which the molar ratio of the 3 compounds was 0.40:0.45:0.15.

Each text was repeated four times and there are reported hereinbelow the average results.

It has to be noted that in tests 3 and 4 sublethal doses of insecticides were used, in order to emphasize the different results obtained by using PBO and a synergistic mixture of the invention.

| TEST | INSECTICIDE | % | SYNERGIST | % | % MORTALITY AFTER 24 HOURS |
|---|---|---|---|---|---|
| 1 A | Bioallethrin | 0.2 | PBO | 0.5 | 55 |
| 1 B | " | 0.2 | PBX.1 | 0.5 | 100 |
| 2 A | Cypermethrin | 0.1 | PBO | 0.5 | 95 |
| 2 B | " | 0.1 | PBX.1 | 0.5 | 100 |
| 3 A | Bioresmathrin | 0.15 | PBO | 0.45 | 15 |
| 3 B | " | 0.15 | PBX.1 | 0.45 | 47 |
| 4 A | Permethrin | 0.15 | PBO | 0.45 | 10 |
| 4 B | " | 0.15 | PBX.2 | 0.45 | 35 |
| 5 A | Propoxur | 1.0 | PBO | 1.0 | 100 |
| 5 B | " | 1.0 | PBX.1 | 1.0 | 100 |
| 6 A | Propetamphos | 0.2 | PBO | 1.0 | 100 |
| 6 B | " | 0.2 | PBX.2 | 1.0 | 100 |

EXAMPLE 3

Larvas of *Heliotis armigera*, well known pest of cotton, were treated with fenvalerate at the dose of 0.2 micrograms/larva. The mortality was 32%. In comparative experiments the larvas were treated with 50 micrograms/larva of piperonylbutoxide 5–15 minutes before fenvalerate was applied. The increase of mortality was 96%.

In other comparative experiments the larvas were treated with 10 micrograms/larva of a mixture of the invention, in which the molar ratio between compounds of formulas (II), (III) and (IV) was 0.43:0.50:0.07. The increase of mortality was 94.5%.

What is claimed is:

1. An insecticidal composition comprising:
   (a) a mixture of methylenedioxybenzene derivatives of the formulae:

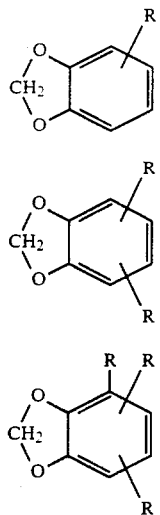

wherein R is $CH_2O(CH_2CH_2O)_2R_1$ and $R_1$ is hydrogen or an alkyl group having 1 to 4 carbon atoms, and (b) an insecticide selected from the group consisting of synthetic pyrethroids, carbamates, organic phosphorates, avermectines, and insect growth regulators, wherein the weight ratio of components (a) and (b) is between 100:1 and 1:1, and wherein in component (a), the ratio of the molar percentages of compound (II):compound (III):compound (IV) is 10-50:30-70:5-20.

2. Insecticide composition according to claim 1, wherein in the compounds of formula (II), (III) and (IV) of component (a) $R_1$ is $C_4H_9$.

3. Method for combating insects which comprises applying to a habitat of the insects an insecticide composition according to claim 1.

4. Method for combating insects which comprises applying to a habitat of the insects an insecticide composition according to claim 2.

* * * * *